United States Patent [19]

Friedrich et al.

[11] Patent Number: 4,909,280
[45] Date of Patent: Mar. 20, 1990

[54] FASTENER FOR CLOSING AND SEALING ENDS OF PIPES SUBJECTED TO INTERNAL PRESSURE

[75] Inventors: Pawel Friedrich; Wiesław Płaczek; Leszek Mynarz; Krzysztof Karpiński; Jerzy Gaszewski, all of Warsaw, Poland

[73] Assignee: Instytut Chemii Przemysłowej, Warsaw, Poland

[21] Appl. No.: 198,120

[22] Filed: May 24, 1988

[30] Foreign Application Priority Data

May 29, 1987 [PL] Poland .................................. 265964
Mar. 10, 1988 [PL] Poland .................................. 271104

[51] Int. Cl.⁴ ........................................... G01M 3/28
[52] U.S. Cl. ........................................ 138/90; 138/89; 73/49.1; 73/49.8
[58] Field of Search ............... 138/89, 90; 73/49.1, 73/49.8, 49.5; 277/34, 2, 27, 73, 72 R; 220/240

[56] References Cited

U.S. PATENT DOCUMENTS

| | | | |
|---|---|---|---|
| 3,434,337 | 3/1969 | Goeke | 73/49.8 |
| 3,886,977 | 6/1975 | Dorgebray | 138/89 |
| 3,963,054 | 6/1976 | Martin | 138/89 |
| 4,077,250 | 3/1978 | Wesch | 138/89 |
| 4,197,733 | 4/1980 | Holland | 73/49.1 |
| 4,766,934 | 8/1988 | Ollivaud et al. | 138/89 |

Primary Examiner—James E. Bryant, III
Attorney, Agent, or Firm—Ladas & Parry

[57] ABSTRACT

A fastener for closing and sealing pipe ends subjected to internal pressure is applicable for testing plastic pipe for internal pressure resistance. Testing is carried out in apparatuses in which a pipe section is filled with water and then pressure is applied, its value corresponding with desired tension in the pipe wall. In the fastener of the invention forces exerting clamping pressure of fastener elements on pipe ends are derived from internal pressure within the pipe, allowing for disengagement of external supply during hours of testing on the one hand, and on the other hand ensuing proper proportion between this pressure and the forces clamping the fastener elements on pipe end.

1 Claim, 1 Drawing Sheet

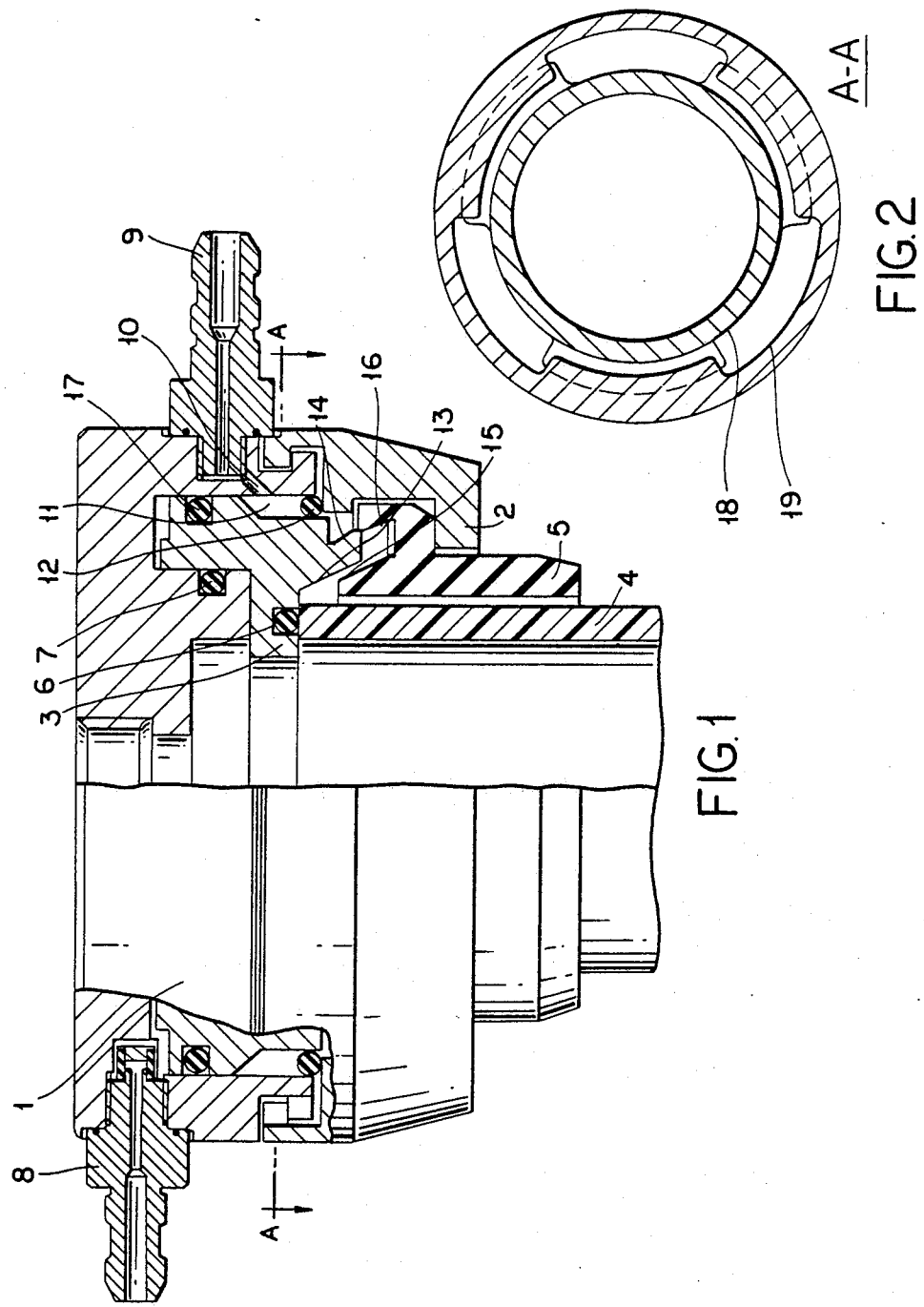

FASTENER FOR CLOSING AND SEALING ENDS OF PIPES SUBJECTED TO INTERNAL PRESSURE

BACKGROUND OF THE INVENTION

1. Field of the Invention

Subject of the invention is a fastener for closing and sealing ends of pipes, for example plastic pipes, subjected to the action of internal pressure and tested in suitable apparatus in which a pipe segment is filled with water and subsequently an increased pressure is established in the pipe, its value corresponding with the required stress in the pipe wall.

2. Description of the Related Art

From the Polish Patent Specification No. 145005 and from the European Patent Application, No. of Publication No. EP-0204270 there is known a hydraulically closed fastener composed of two main parts, namely a cover and a clamp. These two parts are screwed together and thus they enclose a space inside which there are placed a conical elastic sealing and a slidable element. When the fastener has been placed on the pipe end, then the conical ring is at the outside diameter of the pipe under test and the elastic sealing on its end face.

In the cover of the fastener there is located a valve for supplying water to the space between the cover and the movable element. In the cover there is cut out axially a hole for introducing water to the interior of the pipe.

The lower portion of the movable element has a conical surface which cooperates with the conical surface of the elastic ring.

When water has been supplied to the fastener and an increased pressure established in the pipe under test, then the movable element slides in the direction of the end face of the pipe, thus clamping the elastic sealing and the elastic ring. Thus, the fastener becomes fastened on the pipe end, water is supplied into the pipe, an increased pressure is established in it and the relevant test of the internal pressure resistance of the pipe can be carried out.

A drawback of this fastener is the necessity of a continuous supplying of its elements with water to keep the fastener clamped on the pipe during the whole duration of the test, which sometimes reaches 1,000 hours. Moreover, when disassembling the fastener it is often difficult to separate the cover from the clamp due to the seizure of the threads and to the expansion of the conical ring.

From among other designs, a fastener for closing the pipe ends is also known from the Patent Specification of the USSR No. 977968.

This fastener has a cover screwed together with a clamp: inside the clamp there is located a conical clamping ring whereas inside the cover there is a movable conical pin which slides under the action of pressure and seals the pipe end on its internal surface. This surface has been bevelled and against this bevelled surface edge the pin is pressed with its conical surface.

This fastener is suitable both for closing steel pipes and plastic pipes, but only for tests carried out at room temperature, under low pressures and during short periods of time. When these conditions are not met, the pipe material would be destroyed even under low loads applied to it.

A fastener for closing and sealing pipes is also known from the patent Specification of U.S. Pat. No. 3,434,337. In the frame of this fastener there are located several tens of parts, from among which an essential importance for comparing it with the fastener of the present invention have conical elements clamped with a flat element moving under the action of increased pressure from the medium supplied.

This flat element has the shape of a disc with hole which is situated axially on the pipe. Its movement causes a displacement of segments which with their conical surfaces act on the conical surfaces on the next segments and thus clamp them on the pipe. Sealing is realized here by means of a circular packing of the "U"-type situated with its open face to the supplied medium between the external surface of the pipe and internal surface of the sleeve.

This attachment is characterized by a high complexity of its design, is composed of a large number of parts and has considerable dimensions and weight. It makes no separate fastener which can be fastened on the pipe end and placed together with the pipe section in the water tank for the test apparatus, but it makes an integral part of such apparatus.

SUMMARY OF THE INVENTION

The essence of the fastener according to the present invention composed of a cover, a clamp, an elastic conical ring, an elastic packing and a movable element, in which the space between this movable element and the cover is connected with an external supply of water, consists in the fact that this space is subdivided with an elastic packing in two zones, one of them being connected with the external supply and the other with the internal space of the pipe under test. Also the space on the other side of the movable element, it is the space between this element and the clamp, is connected with the external supply. Both parts cooperating with each other, namely the movable element and the elastic ring, besides the conical surfaces cooperating with each other during pushing the movable element to the end face of the pipe under test, that results in clamping the elastic ring on the pipe. Also other conical surfaces cooperating with each other during pushing away the movable element from the end face of the pipe, that results in the expansion of the elastic ring.

"The fastener of the invention is characterized with the fact that forces which exert clamping pressure on fastener members at the end of the pipe under test are derived from internal pressure existing in the pipe, thus allowing disengagement of an external supply during hours of testing on the one hand, and on the other hand it ensures proper proportion between this pressure and the forces clamping the fastener elements around the pipe. This effect results from connecting the internal pipe space with respective space between movable element and cover. After clamping the fastener elements with the use of a preliminary force deriving from the external supply and filling the sample under test with water, further clamping function is taken over by pressure of water filling the pipe. Thus, any superflous loads which negatively influence the pipe sections and deform their ends excessively, may be avoided."

The most important advantage of the design of fastener according to this invention results from the connection between the internal space of the pipe under test and the corresponding space between the movable element and the cover, as after clamping the fastener elements with a preliminary force deriving from the external supply and filling the pipe section with water, the function of maintaining the fastener elements in the clamped condition is taken over by the pressure of water filling the pipe. This means that it is sufficient to clamp the fastener elements preliminarily even with a small force and thereupon the force of clamping the fastener changes proportionally to the pressure of water filling the pipe, it means to the internal pressure under which the pipe is tested. Thus, any superfluous loads which negatively influence the pipe sections and deform excessively their ends, are avoided.

The fastener may easily and rapidly be mounted or dismounted on the pipe and easily disassembled. To take away the fastener from the pipe it is enough after having finished the test to apply the water pressure to the space between the movable element and the clamp, thus displacing the movable element in the direction from the end face of the pipe and causing expansion of the elastic clamping ring. Also the operation of connecting and disconnecting the two parts of the fastener, the cover and the clamp, is very easy due to the bayonet coupling design.

BRIEF DESCRIPTION OF THE DRAWING

FIG. 1 is a side view of the apparatus of the present invention in partial section;

FIG. 2 is a cross section of the apparatus of FIG. 1 along the section line A-A.

DESCRIPTION OF THE PREFERRED EMBODIMENT(S)

Referring to FIGS. 1 and 2, the present invention is shown schematically in its construction.

The fastener is composed of a cover 1 and a clamp 2 inside which there is a movable element 3 in the shape of a ring. This element is placed slideably in the cover 1. Inside the clamp 2 and on the external surface of the pipe under test 4 there is an elastic conical clamping ring 5. On the end face of the pipe under test 4 there is an elastic packing 6 and the space between the movable element 3 and the cover 1 is subdivided with the packing 7 in two zones. One zone is connected with the internal space of the pipe under test 4 and the other zone via valve 8 with an external supply of the fastener with water, with which supply via valve 9 and passage 10 there is also connected the space between the movable element 3 and the clamp 2 cover 1. This space is tightened with the packing 12. In the movable element 3 there are machined conical surfaces 13 and 14 and in the elastic ring 5 - conical surfaces 15 and 16. The surfaces 13 and 15 cooperate with each other during the process of clamping the fastener on the pipe 4, whereas the surfaces 14 and 16 during dismounting the fastener from the pipe 4. On the surface of the movable contact of the element 3 with the cover 1 there is place the elastic packing 77. In the cover 1 and in the clamp 2 there are made cut-outs corresponding with each other, which cut-outs are in each part displaced one in relation to the other by a constant angular spacing.

"After feeding water to the fastener via valve 8 and building up pressure, water passes into the space closed in between cover 1, movable element 3 and seals 17 and 7, causing the element 3 to move relatively to cover 1. This results in surface 14 moving away from surface 16 and surface 13 starting to cooperate with surface 15. Movement of element 3 causes a reduction in the internal diameter of ring 5 until it meets the pipe wall 4. Thus the fastener is preliminarily clamped.

The force exerted by internal pressure to which the pipe under test is subjected, influences the surface limited by seal 6, aiming at slipping the ring off the pipe. At the same time this force acts on the other side of element 3, both on the surface limited by seal 6, and on the surface closed between seals 6 and 7, causing constriction of ring 5. The clamping force is then greater than the decompressing ring 5.

In order to remove the fastener from the pipe, valve 8 is screwed off or loosened, and water is fed via valve 9 and passage 10 into the space closed in between cover 1, element 3 and seals 17 and 12. Water pressure forces the element 3 to retract, conical surface 13 to move away from surface 15 and surface 14 to engage with surface 16 causing widening of the internal diameter of ring 5. Movement of element 3 goes on till it meets cover 1.

The fastener of the invention is applied in testing plastic pipes for internal pressure resistance. Testing is carried out in appropriate apparatus, where a pipe section is filled with water and then applied pressure is added, its value corresponding with desired tension in the pipe wall."

We claim:

1. A fastener for closing and sealing ends of pipes subjected to internal pressure comprising two disconnectably connected parts a cover and a clamp inside which there is located an elastic, conical ring to be clamped on the pipe and between this ring and the cover there is a movable element in the shape of a ring which possesses a conical surface cooperating with the conical surface of the elastic ring during sliding the movable element to the end face of the pipe, and between this movable element and the end face of the pipe under test there is placed an elastic packing, and the space between the cover and the movable element is connected with an external supply of water, wherein the space is divided with the use of flexible seal into two zones, one of which is connected with external water supply source and the second with the internal space of pipe under testing wherein the external supply source is also connected with space, situated on the other side of movable element, the space between this element and clamp, the movable element and resilient ring having additional conical surfaces.

* * * * *